(12) United States Patent
Nandi et al.

(10) Patent No.: US 11,827,587 B2
(45) Date of Patent: *Nov. 28, 2023

(54) CATALYTIC PARTIAL OXIDATION OF METHANE

(71) Applicant: ExxonMobil Technology and Engineering Company, Annandale, NJ (US)

(72) Inventors: Partha Nandi, Annandale, NJ (US); Steven L. Suib, Storrs, CT (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 281 days.

This patent is subject to a terminal disclaimer.

(21) Appl. No.: 17/236,496

(22) Filed: Apr. 21, 2021

(65) Prior Publication Data

US 2021/0331992 A1 Oct. 28, 2021

Related U.S. Application Data

(60) Provisional application No. 63/014,579, filed on Apr. 23, 2020.

(51) Int. Cl.
*C07C 29/50* (2006.01)
*B01J 27/24* (2006.01)
*B01J 3/00* (2006.01)

(52) U.S. Cl.
CPC .............. *C07C 29/50* (2013.01); *B01J 3/008* (2013.01); *B01J 27/24* (2013.01); *B01J 2219/00051* (2013.01); *B01J 2219/00166* (2013.01); *C07C 2527/24* (2013.01)

(58) Field of Classification Search
CPC ..... C07C 29/50; C07C 2527/24; C07C 31/04; C07C 31/08
See application file for complete search history.

(56) References Cited

U.S. PATENT DOCUMENTS

| 10,099,979 | B2 * | 10/2018 | Román-Leshkov .... C07C 29/50 |
| 2015/0099876 | A1 | 4/2015 | Chan et al. |
| 2019/0185397 | A1 | 6/2019 | Nandi et al. |

OTHER PUBLICATIONS

Grant, J. T. et al., (2016) "Selective oxidative dehydrogenation of propane to propene using boron nitride catalysts", Science, vol. 354, No. 6319, pp. 1570-1573.

(Continued)

*Primary Examiner* — Jafar F Parsa
(74) *Attorney, Agent, or Firm* — SHOOK, HARDY & BACON L.L.P.

(57) ABSTRACT

Systems and methods are provided for direct conversion of methane and/or ethane to methanol. The methods can include exposing methane to an oxidant, such as $O_2$, in a solvent at conditions that are supercritical for the solvent while having a temperature of 310° C. or less, or about 300° C. or less, or about 290° C. or less. The solvent can correspond to an electron donor solvent that, when in a supercritical state, can complex with $O_2$. By forming a complex with the $O_2$, the supercritical electron donor solvent can facilitate conversion of alkane to methanol at short residence times while reducing or minimizing further oxidation of the methanol to other products.

20 Claims, 1 Drawing Sheet

(56) References Cited

OTHER PUBLICATIONS

Shi, L., (2017) "Edge-hydroxylated Boron Nitride for Oxidative Dehydrogenation of Propane to Propylene", ChemCatChem, vol. 9, No. 10, pp. 1788-1793.

Theyssen, N. et al., (2006) "Selective oxidation of alkanes with molecular oxygen and acetaldehyde in compressed (supercritical) carbon dioxide as reaction medium", Chemistry—A European Journal, vol. 12, pp. 3401-3409.

* cited by examiner

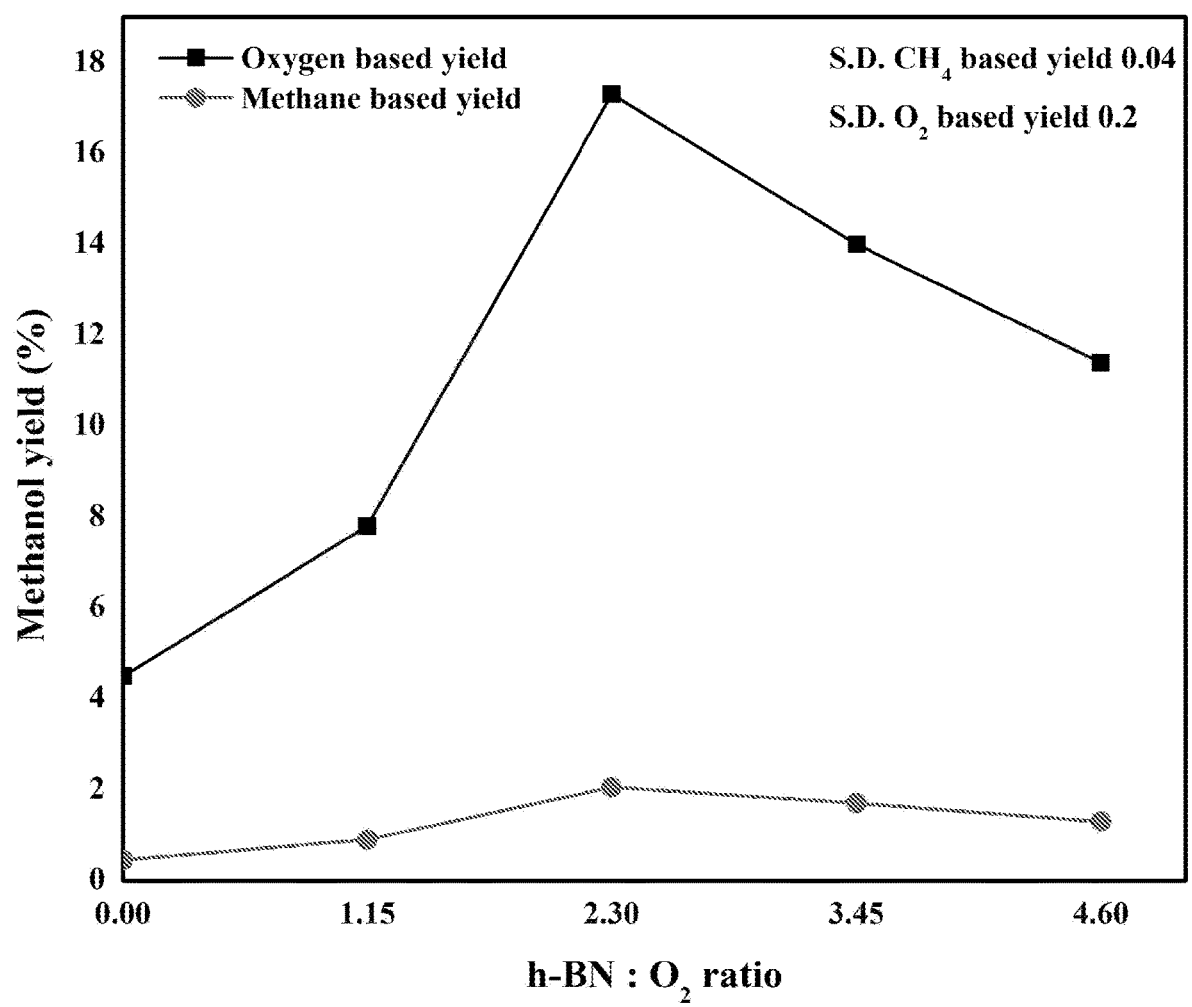

CATALYTIC PARTIAL OXIDATION OF METHANE

PRIORITY

This application claims priority to and the benefit of U.S. Provisional Application No. 63/014,579, filed Apr. 23, 2020, the disclosure of which is incorporated herein by reference in its entirety.

FIELD OF THE INVENTION

Embodiments of the invention relate to catalytic partial oxidation of methane and/or ethane to methanol.

BACKGROUND

The ability to directly convert methane to methanol is strongly desirable from an economic perspective. Current natural gas supplies can typically include about 95% of $CH_4$. Unfortunately, transportation of natural gas is roughly twice as expensive as transport of typical liquid fuels. Such transport costs can account for up to 40% to 80% of the price of natural gas and/or methane.

Thermodynamically, the partial oxidation of methane to methanol appears to be a favorable reaction. It has been a challenge, however, to directly oxidize methane with air as an oxidant. The C—H bond in methane is stronger than the C—H bond strength of methanol. Hence it has been impossible using conventional methods to stop the oxidation reaction at the stage of partial oxidation to methanol in any significant yield. Instead, further oxidation of methanol to formaldehyde, formic acid, CO and $CO_2$ happens readily in conventional gas phase reactors.

Alternatively, in a large capital intensive process involving an indirect conversion reaction pathway, methane can be converted into syngas which can subsequently be converted into either methanol or to a mix of hydrocarbons (Gas to Liquid or GTL plant) via a Fischer-Tropsch process. While this type of indirect method can be effective for conversion of methane to methanol, the capital-intensive nature of the process can substantially reduce the benefit of being able to convert the methane to methanol and/or other products. For example, indirect conversion of methane to methanol typically involves multiple reactions requiring distinct high temperature, high pressure environments. Maintaining each reaction environment at the correct temperature and/or pressure to perform the net conversion reaction can require substantial resources. A new alternative to directly convert methane to methanol remains an unmet need in this area.

U.S. Patent Application Publication No. 2015/0099876 describes a method for oxidizing hydrocarbons based on molecular catalysts. The method involves exposing a hydrocarbon to a tri-copper cluster catalyst in the presence of hydrogen peroxide in an acetonitrile solvent. The hydrogen peroxide is consumed during the reaction cycle. Although methane is described as a potential hydrocarbon for oxidation, only a modest conversion for oxidation of methane to methanol is shown in the examples. A method that can provide oxidation of methane to methanol with improved conversion rates and/or that can avoid the need for hydrogen peroxide as a reagent would be desirable. More generally, a process that can reduce or minimize the need for specialized catalysts and/or the need for reagents that are comparable to or more expensive than methane is desirable.

SUMMARY OF THE INVENTION

In an aspect, a method for partial oxidation of ethane is provided. The method includes contacting ethane with $O_2$ in the presence of acetonitrile in a reaction environment, under supercritical conditions for acetonitrile, to form methanol and ethanol. The supercritical conditions can include a temperature of 310° C. or less, or 300° C. or less. In some aspects, a molar amount of ethanol formed can be greater than a molar amount of methanol formed. Optionally, the ethane can be contacted with $O_2$ in the absence of a catalyst.

In another aspect, a method for partial oxidation of alkanes is provided. The method includes contacting methane, ethane, or a combination thereof with $O_2$ in the presence of acetonitrile and boron nitride in a reaction environment, under supercritical conditions for acetonitrile, to form methanol. The supercritical conditions can include a temperature of 300° C. or less. In some aspects, the boron nitride is supported on graphite, $SiO_2$, molybdenum sulfide, tungsten sulfide, carbon nanotubes, nitrogen-doped carbon nanotubes, or a combination thereof. Additionally or alternately, in some aspects a ratio of initial surface area of the boron nitride to a molar amount of $O_2$ in the reaction environment is 4.5 to 7.0 $m^2$ BN (SA)/mmole $O_2$. In some aspects, a molar amount of ethanol formed can be greater than a molar amount of methanol formed.

BRIEF DESCRIPTION OF THE FIGURES

The FIGURE shows yield of methanol relative to methane concentration and $O_2$ concentration for various amounts of boron nitride catalyst.

DETAILED DESCRIPTION OF THE INVENTION

In various aspects, systems and methods are provided for direct methane conversion to methanol. The methods can include exposing methane to an oxidant, such as $O_2$, in a solvent at conditions that are substantially supercritical for the solvent while having a temperature of about 310° C. or less, or about 300° C. or less, or about 290° C. or less. The solvent can correspond to an electron donor solvent that, when in a supercritical state, can complex with $O_2$. By forming a complex with the $O_2$, the supercritical electron donor solvent can facilitate conversion of methane to methanol at short residence times while reducing or minimizing further oxidation of the methanol to other products. It is noted that sub-critical conditions (either pressure or temperature below the critical point) do not appear to lead to the increased oxidation of methane to methanol as described herein.

In various aspects, it has also unexpectedly been discovered that ethane can be converted to methanol by direct oxidation with $O_2$. During direct oxidation of ethane, it has further been unexpectedly discovered that ethanol can be formed with greater yield than methanol. In ethane, the bond enthalpy for a carbon-hydrogen bond is roughly 410 kJ/mol, while the bond enthalpy for the carbon-carbon bond is roughly 370 kJ/mol. Due to this roughly 40 kJ/mol difference, it was expected that direct oxidation would be strongly selective for breaking of the carbon-carbon bond, resulting in preferential formation of methanol rather than ethanol. However, it has been discovered that the direct oxidation environment described herein allows for formation of ethanol in greater yield than methanol.

In some aspects where ethane is included in the reaction environment, the molar ratio of ethane to methane in the reaction environment and/or in the hydrocarbon feed to the reaction environment can be 4.0 or more (i.e., a 4:1 molar ratio), or 6.0 or more, or 8.0 or more. It is noted that in the limiting case, the reaction environment may include no methane. Having a molar ratio of ethane to methane of 4.0 or more in the reaction environment is defined herein to include the limiting case of having no methane in the reaction environment.

In other aspects, the reaction environment can be substantially free of $C_{2+}$ hydrocarbons, so as to reduce or minimize competing side reactions to form oxygenated $C_{2+}$ side products. A reaction environment that is substantially free of $C_{2+}$ hydrocarbons can correspond to a reaction environment where the molar amount of $C_{2+}$ hydrocarbons is less than 1% of the molar amount of methane, or less than 0.1%.

In various aspects, it has further unexpectedly been discovered that the conversion of methane and/or ethane to methanol in the presence of $O_2$ can be improved or facilitated by decreasing the available oxygen content for oxidation. Conventionally, the relative concentration of methane to $O_2$ in the reaction environment has represented a trade-off between increased conversion (of any type) of methane versus increased additional oxidation of methanol (after initial conversion) to other products. Conventionally, this trade-off has limited the yield of methanol to less than 1 mole % relative to the molar amount of $O_2$ in the reaction environment.

By contrast, the methods described herein related to using an electron donor solvent under supercritical conditions can allow for increased conversion of methane and/or ethane based on increasing the ratio of methane to $O_2$. Without being bound by any particular theory, it is believed that the supercritical solvent reaction environment can provide solvent clusters for activation of $O_2$ (via specific solute-solvent interactions) to enable methane oxidation and/or ethane oxidation while expanding the residence time window for increased or improved recovery of methanol (and optionally ethanol) as the oxidation product. Based on the increased reactivity of the activated $O_2$, it is believed that the residence time window for recovery of methanol and/or ethanol can be further increased by decreasing the concentration of $O_2$, while still providing an overall improvement in the yield of methanol, the yield of ethanol, or the combined yield of methanol and ethanol, relative to the amount of oxygen in the reaction environment. This improved yield relative to the amount of oxygen can provide other potential benefits, such as potentially improving the yield relative to the amount of methane (and/or ethane) and/or reducing or minimizing the loss of methane and/or ethane to other conversion products. In some aspects, the molar ratio of methane to $O_2$ can be 2.0 or more, or 4.0 or more, or 8.0 or more, or 15 or more, such as up to 50 or possibly still higher. Additionally or alternately, in some aspects, the molar ratio of ethane to $O_2$ can be 2.0 or more, or 4.0 or more, or 8.0 or more, or 15 or more, such as up to 50 or possibly still higher. Further additionally or alternately, in some aspects a molar ratio of the combined amount of methane and ethane to $O_2$ can be 2.0 or more, or 4.0 or more, or 8.0 or more, or 15 or more, such as up to 50 or possibly still higher.

The electron donor solvent can correspond to a non-aqueous solvent. Although water may be present, it is undesirable from both a reaction standpoint and from a product recovery standpoint to have excess water in the reaction environment. From a reaction standpoint, water typically serves as a proton donor/electron acceptor, and therefore is not suitable for playing a role as an electron donor solvent. From a product recovery standpoint, methanol is miscible in water and is difficult to fully recover using simple distillation. Thus, it can be beneficial to form methanol in a reaction environment that has a reduced or minimized amount of water. In various aspects, water can correspond to 10 mole % or less of the reaction environment, or 1.0 mole % or less, or 0.1 mole % or less, such as down to having substantially no water content (0.01 mole % or less). The amount of water can preferably be less than the amount of the electron donor solvent.

Instead of using water, examples of electron donor solvents can include solvents such as $CO_2$, acetonitrile, and various halogenated derivatives of acetonitrile. It is noted that $CO_2$ and acetonitrile may sometimes be referred to as examples of weak electron donor solvents. In addition to being electron donors, these examples of electron donor solvents also have a critical point temperature of about 310° C. or less, or about 300° C. or less, or about 290° C. or less. In various aspects, improved yields of methanol from methane and/or ethane can be achieved in an electron donor solvent at supercritical conditions. However, at temperatures of about 300° C. or more, methanol can readily oxidize to $CO_2$ and $H_2O$ in the presence of an oxidant. Maintaining the reaction environment at supercritical conditions while staying below about 310° C., or below about 300° C., or below about 290° C., can facilitate oxidation of methane and/or ethane to methanol while reducing or minimizing the direct oxidation of the methanol to $CO_2$. In various aspects, relative to the total moles of conversion products, the selectivity for $CO_2$ production can be 50 mole % or less, or 30 mole % or less, or 20 mole % or less, such as down to 1 mole % or possibly still lower.

In various aspects, oxidizing methane and/or ethane to methanol in a supercritical solvent corresponding to an electron donor can allow for methanol yields, relative to oxygen ($O_2$) present in the reaction environment, of 1.0 mole % or more, or 2.0 mole % or more, or 5.0 mole % or more, or 10 mole % or more, such as up to 25 mole % or possibly still higher. The molar ratio of solvent to oxygen in the reaction environment can optionally but preferably be 5.0 or more, or 8.0 or more, such as up to 50 or possibly still higher. It is noted that in some aspects, air can be a convenient source of $O_2$. The upper limit on the molar ratio of solvent to oxygen can be related to practical issues, such as being able to perform the reaction without requiring excessive volumes for the reaction environment. In various aspects, oxidizing methane to methanol in a supercritical solvent corresponding to an electron donor can allow for methanol yields, relative to methane present in the reaction environment, of 0.7 mole % or more, or 0.9 mole % or more, or 1.2 mole % or more, such as up to 3.5 mole % or possibly still higher.

Acetonitrile is an example of a suitable solvent for use at supercritical conditions for oxidation of methane to methanol. The critical temperature and pressure for acetonitrile are 272° C. and 4.87 MPa-a.

In some aspects, the oxidation of methane and/or ethane can be performed in the absence of a catalyst, such as in the absence of an initiator. In other aspects, a minor amount of an initiator can be used to further increase the yield of oxygen. Some initiators can correspond to fluids that are introduced into the reaction environment, while other initiators can correspond to solid compounds. An example of an initiator compound that can be introduced as a fluid into the reaction environment is hydrogen peroxide. Fluid initiator compounds can be included in the reaction environment in sub-stoichiometric amounts. For example, the molar amount of initiator can be 70% or less relative to the molar amount of oxygen, or 50% or less, or 30% or less, or 10% or less, such as down to 1% or possibly still lower.

In other aspects, a solid nitride such as boron nitride can be used as a solid phase initiator. Other examples of solid nitrides can include, but are not limited to indium nitride, titanium nitride, gallium nitride, Group 13 metal nitrides, and combinations thereof. It has been discovered that an unexpected improvement yield improvement can be achieved by providing a relatively narrow range of available surface (or near-surface) initiation sites in comparison with the available amount of oxygen in the reaction environment. It is believed that the amount of available initiation sites is approximated by the available initial surface area of the initiator.

Definitions

In this discussion, direct conversion of methane and/or ethane to methanol is defined as a conversion process where the exposure of the methane and/or ethane to a single reaction environment results in production of methanol. This is in contrast to indirect conversion methods, where two or more reaction environments are used. During indirect conversion, in a first reaction environment, methane (and/or ethane) is converted to one or more intermediates, and then the intermediate(s) are converted in a second reaction environment that has one or more differences relative to the first reaction environment. The one or more differences can correspond to a difference in temperature of at least 5% (relative to the temperature in Kelvin of the first environment); a difference in pressure of at least 5%; the presence of absence of a catalyst; the presence or absence of a reagent; or a combination thereof.

In this discussion, supercritical conditions refer to conditions that correspond to supercritical conditions for the solvent used in the reaction system. Acetonitrile is an example of a solvent. It is understood that adding diluents to a solvent (such as methane, ethane, and oxygen) can produce a system with a modified phase diagram. However, for purposes of clarity in defining the reaction conditions, all references to supercritical conditions correspond to the pure phase of the solvent. Thus, when referring to supercritical conditions (or substantially supercritical conditions) for acetonitrile, it is understood that this corresponds to supercritical conditions for pure phase acetonitrile, which has a critical temperature of 272° C. and a critical pressure of 4.87 MPa-a.

In this discussion, substantially supercritical conditions for a solvent are defined as conditions where one of the temperature and pressure of the reaction environment are beyond the critical point, while the other of the temperature and pressure are within 5 percent of the critical point. For instances where the pressure is beyond the critical point pressure, the temperature can be different from the critical point temperature by less than 5% (in Kelvin).

In this discussion, a reaction environment is defined as a contiguous volume that has supercritical conditions or substantially supercritical conditions for the solvent.

In this discussion, a solvent refers to a compound present in the reaction environment a) that is present in a molar amount that is greater than the molar amount of oxygen, and b) that is not consumed during the oxidation reaction to convert methane to methanol. Thus, a solvent corresponds to a compound that is substantially non-reactive under in the reaction environment under conditions where the solvent is supercritical. Examples of solvents include, but are not limited to, acetonitrile, carbon dioxide, tricholoroacetonitrile, fluoroacetonitrile, trifluoroacetonitrile, and combinations thereof.

In this discussion, the residence time can refer to the average amount of time that methane and/or ethane is exposed to oxygen under supercritical conditions or under at least one of supercritical conditions and substantially supercritical conditions. In various aspects, the residence time can correspond to 10 minutes or less, or 1.0 minutes or less, or 0.1 minutes or less. In various aspects, the residence time can correspond to 0.1 seconds or more, or 1.0 seconds or more, or 10 seconds or more, or 1.0 minutes or more. In some aspects, the residence time a) under supercritical conditions or b) under at least one of supercritical conditions and substantially supercritical conditions can be 0.1 seconds to 10 minutes, or 0.1 seconds to 1.0 minutes, or 1.0 seconds to 1.0 minutes, or 10 seconds to 10 minutes, or 10 seconds to 1.0 minutes.

In this discussion, reference will be made to an initial surface area for nitride initiators in a reaction environment, such as a boron nitride initiator. The initial surface area is defined as the surface area for a nitride material when first loaded into a reaction environment. This surface area may change after exposure of the nitride material to supercritical reaction conditions. It has been confirmed that the initiator benefits described herein are retained when boron nitride is exposed to supercritical reaction conditions, the supercritical reaction conditions are removed, and then the supercritical reaction conditions are introduced again.

In this discussion, reference will be made to a ratio of initial surface area for boron nitride and/or another nitride initiator in a reaction environment relative to the amount of $O_2$ in the reaction environment. This ratio has the units of meters square of initial boron nitride surface area in the reaction environment relative to the millimoles of $O_2$ present in the reaction environment. In this discussion, the units for this ratio can be denoted as $<m^2$ XN (SA)/mmole $O_2>$, where X corresponds to boron, indium, titanium, gallium, a Group 13 metal, or a combination thereof. For example, for boron nitride, the units for this ratio can be denoted as $<m^2$ BN (SA)/mmole $O_2>$.

In this discussion, references to the Periodic Table correspond to the current version of the IUPAC Periodic Table.

Cluster Formation and Supercritical Solvent

Without being bound by any particular theory, it is believed that using a supercritical electron donor solvent can facilitate oxidation of methane to methanol by forming complexes with the $O_2$. The complexes can potentially provide several benefits. One type of benefit can correspond to activation of $O_2$ molecules. For example, it is believed that $O_2$ molecules can interact with clusters of solvent molecules and become partially polarized. This partial polarization can facilitate breaking the $O_2$ bond so that the $O_2$ can react with methane to form methanol. Additionally or alternately, another type of benefit can correspond to modulating the local concentration of $O_2$. Conventionally, one of the difficulties with oxidizing methane (and/or ethane) with $O_2$ is stopping the oxidation reaction at methanol. Under conventional conditions for methane oxidation, once methane starts the oxidation process, the reaction products can tend to oxidize past methanol to another product, such as formaldehyde or $CO_2$. Similar difficulties in stopping the reaction at an alcohol can be encountered conventionally during ethane oxidation. Without being bound by any particular theory, it is believed that the association of $O_2$ with the solvent clusters can reduce or minimize local concentration variations. This can increase the residence time window where alcohols can be formed and then removed from the reaction environment without further oxidation to other products.

It is believed that the ability to form reduced or minimized energy solvent clusters can contribute to the ability to activate oxygen and/or moderate oxygen concentration variations within the solvent environment. It is further believed that this cluster formation can be enhanced by using a solvent under supercritical conditions. Under supercritical conditions, the phase boundary between a liquid phase and a gas phase is not present. Instead, a continuous fluid phase is present beyond the supercritical point for a solvent. The absence of a gas-liquid phase transition is indicative of a fluid state where individual molecules are close enough together to form clusters while having sufficient energy to escape local minima and potentially spend substantial time in cluster states with favorable energy.

In order to further investigate the interaction of solvent clusters and oxygen, density functional calculations were performed on a variety of solvent clusters. The calculations corresponded to density functional theory (DFT) calculations performed at the B3LYP/6-311++G(d,p), to determine local energy minima for various cluster sizes (2-16 molecules) of acetonitrile compounds. After determining the lowest energy configurations at the various cluster sizes, dipole moments for each cluster were determined. The results of the calculations are shown in Table 1, along with the corresponding dipole moment calculated by DFT for a single acetonitrile molecule.

TABLE 1

Dipole Moment of Optimized Acetonitrile Clusters

| Cluster size, n | Dipole moment (Debye) |
|---|---|
| $CH3CN$ (n = 1) | 4.0534 |
| $(CH3CN)_2$ (n = 2) | 0.001 |
| $(CH3CN)_3$ (n = 3) | 0.0026 |
| $(CH3CN)_4$ (n = 4) | 0.0005 |
| $(CH3CN)_5$ (n = 5) | 0.2028 |
| $(CH3CN)_6$ (n = 6) | 0.0016 |
| $(CH3CN)_8$ (n = 8) | 0.0134 |
| $(CH3CN)_{12}$ (n = 12) | 1.0243 |
| $(CH3CN)_{16}$ (n = 16) | 0.0544 |

As shown in Table 1, with the exception of the n=12 cluster, the dipole moment for the lowest energy cluster for each cluster size was close to zero. This is in contrast to the dipole moment of roughly 4 Debye for a single acetonitrile cluster. Without being bound by any particular theory, it is believed that under supercritical conditions, the molecular configurations for an acetonitrile solvent include a substantial contribution from minimum energy clusters that also have a reduced or minimized dipole moment.

Additional DFT calculations were performed for incorporation of an $O_2$ molecule into acetonitrile clusters. In Table 2, results are shown from determining minimum energy configurations for $O_2$ in a cluster including n=4, 5, or 6 acetonitrile molecules. The configuration for the acetonitrile molecules at the start of optimization roughly corresponded to the minimum energy configuration for the cluster without the presence of $O_2$. The results in Table 2 show the charge on each oxygen atom in the $O_2$ molecule when incorporated into the n=4, 5, or 6 clusters.

TABLE 2

Charge on Oxygen Atoms for $O_2$ in Acetonitrile Clusters

| Cluster-O2 | Charge on Oxygen1 | Charge on Oxygen2 |
|---|---|---|
| $(CH3CN)_4$-$O_2$ | 0.08 | −0.03 |
| $(CH3CN)_5$-$O_2$ | 0.095 | −0.029 |
| $(CH3CN)_6$-$O_2$ | 0.07 | −0.02 |

As shown in Table 2, incorporation of $O_2$ into the acetonitrile clusters resulted in an asymmetric charge distribution between the oxygen atoms in the $O_2$. It is believed that this polarization of the $O_2$ can contribute to activation of the $O_2$ for reaction with methane to form methanol. With regard to details for the minimum energy configurations, in the tetramer (n=4) and pentamer (n=5) clusters, the $O_2$ was interacting with 2 of the hydrogen bonded interactions in the acetonitrile clusters (i.e., an interaction between C—H at one end of a first molecule and N from a second molecule) leading to polarization of $O_2$. In the case of the hexamer cluster (n=6), oxygen was interacting via hydrogen bonds with hydrogens that were not involved in intermolecular interactions of the hexamer cluster.

Example Configuration

To illustrate the benefits of performing methane oxidation to methanol at supercritical solvent conditions, a test apparatus was constructed. In the test apparatus, a reactor controller (such as a controller that includes a PID controller) was used to control the temperature in a reactor via a heater. The reactor corresponded to a reactor that was suitable as a reaction environment at temperatures of up to roughly 300° C. and pressures of up to roughly 15 MPa-g. An example of a suitable reactor is a high pressure reactor (50 mL) available from Parr Instruments. The reactor vessel included inputs for introducing gases from a nitrogen source, an oxygen source, and one or more of a methane source and an ethane source. Any other components in the reaction environment (such as solvent and/or initiator) were introduced into the reactor directly prior to sealing the reactor. The reactor controller monitored the conditions in the reactor via a thermocouple and a pressure sensor. Optionally, a helium source could have been used in place of or in addition to the nitrogen source. The system further included a liquid nitrogen source to allow for cooling of the reactor during introduction of the oxygen and methane into the reaction environment.

In a typical reaction, solvent and any optional catalyst/initiator/other reagents were loaded to the reactor. The reactor was then cooled down to −35° C. by use of liquid nitrogen and pressurized with desired amount of $O_2$, alkane ($CH_4$ or $C_2H_6$) and neutral gas ($N_2$ or He) while the temperature was stable at −35° C. Then the reactor was heated to a temperature in the range of 250° C.-300° C., or 275° C.-300° C., with a ramp rate of 2.5° C./min and the desired dwelling time. The dwelling time at the final temperature was typically either 0 minutes (no dwell time) or 3 minutes. The reactor was then cooled down to ambient temperature by natural convection. The products were analyzed by GC-MS (gas chromatography-mass spectrometry) and NMR to determine methanol concentration. It is noted that the reactor described herein corresponded to a batch reactor. However, the reactions described herein can alternatively be performed in a continuous reaction environment. It is further noted that the benefits of low dwell time shown below can in some ways be more readily achieved in a continuous reaction environment.

Example 1

Oxidation Under Supercritical Solvent Conditions

The experimental procedure described above was used to expose methane to $O_2$ in the presence of acetonitrile as a solvent under various conditions as shown in Table 3. 3 mL (57 mmol) of acetonitrile was loaded into the reactor. $CH_4$, $O_2$, and $N_2$ were then fed into the reactor at a temperature of −35° C. The amount of $CH_4$ was 77 mmol while the $O_2$ was 19 mmol. This corresponded to a molar ratio of $CH_4$ to $O_2$ of roughly 3.8. $N_2$ was then added to provide roughly the desired pressure when the final temperature of 300° C. was reached. As shown in Table 3, the pressure and temperature were varied to perform the experiment under conditions that corresponded to supercritical acetonitrile, substantially supercritical acetonitrile, and traditional gas or liquid phase acetonitrile. The methanol yield corresponds to moles of methanol produced relative to moles of $O_2$ in the reaction environment.

TABLE 3

Methane Oxidation in Supercritical and Sub-Supercritical Acetonitrile

| Phase | Pressure (MPa-a) | T (° C.) | MeOH Yield (mol %) |
|---|---|---|---|
| Ambient | 0.1 | 300 | 0 |
| Subcritical | 2.8 | 300 | 0 |
| Supercritical | 5.6 | 300 | 1.0 |
| Supercritical | 8.4 | 300 | 1.5 |
| Supercritical | 8.4 | 275 | 1.3 |
| Subcritical | 8.4 | 250 | 0.1 |

As shown in Table 3, the first two pressure and temperature combinations were at pressures below the critical point for acetonitrile (less than 4.87 MPa-a), while the final condition was at a temperature below the critical point for acetonitrile (272° C.). At pressures below the critical point, no methanol formation was observed. At substantially supercritical combination of 8.4 MPa-a and 250° C., a small amount of methanol formation was observed. However, the amount of methanol yield was an order of magnitude lower than the methanol yield for the supercritical conditions.

It is noted that some of the supercritical conditions shown in Table 3 were repeated using fully deuterated acetonitrile ($CD_3CN$). When using fully deuterated acetonitrile, no deuterium was incorporated into the methanol product. This indicates that the supercritical solvent was facilitating the reaction without serving as a reagent.

Example 2

Methane to Oxygen Ratio

In this example, 3 mL (57 mmol) of acetonitrile loading to the reactor and cold fed (−35° C.) with desired $O_2$, $CH_4$ and sufficient neutral gas to achieve a target pressure of 10 of roughly 10 MPa-a at −35° C. This resulted in pressures of roughly 28 MPa-a at the final temperature of 300° C. The amounts of $O_2$ and $CH_4$ were varied as shown in Table 4 to provide various molar ratios of $CH_4:O_2$. The reactor was then heated with a ramp rate of 2.5° C./min up to 300° C. and then cooled to ambient (no dwell time) at natural convection rate. In Table 4, the methanol yield is reported as a yield relative to both the moles of $O_2$ and the moles of $CH_4$. The resulting molar concentration of $CH_3OH$ in the reactor was also determined. It is noted that multiple tests were performed at some reaction conditions. For conditions were several test results were available, the results were averaged and error bars were calculated for the result.

TABLE 4

Methane to Oxygen Ratio

| $CH_4$ (mmol) | $O_2$ (mmol) | Ratio of $CH_4:O_2$ | MeOH yield (%) $O_2$ based | MeOH yield (%) $CH_4$ based | MeOH Concentration (M) |
|---|---|---|---|---|---|
| 11 | 22 | 0.5 | 0.1 | 0.3 | 0.01 |
| 71 | 19 | 3.7 | 2.6 | 1.4 | 0.33 |
| 118 | 13.5 | 8.7 | 4.1 | 0.94 | 0.37 |
| 118 | 7 | 16.8 | $6^{+/-0.8}$ | 0.71 | 0.28 |
| 181 | 3 | 60.3 | 5.0 | 0.16 | 0.1 |

As shown in Table 4, increasing the molar ratio of $CH_4$ to $O_2$ resulted in increased amounts of methanol formation for ratios up to roughly 9:1 or 10:1. At $CH_4$ to $O_2$ molar ratios greater than 15:1, the yield relative to $O_2$ may still be higher, but the relative lack of $O_2$ in the environment means that the yield relative to $CH_4$ starts to decline for molar ratios greater than about 5:1. At molar ratios of 15:1 or higher, the decline in methanol yield can also cause the net concentration of methanol reaction environment after conversion to be lower.

It is noted that all of the methanol yields about 1.0 mol % relative to the amount of $O_2$ are unexpectedly high. Conventionally, reducing the amount of $O_2$ would be expected to a decrease in both conversion to methanol and conversion to any type of product, with yield relative to amount of $O_2$ being relatively constant. By contrast, it is believed that the supercritical solvent environment can activate $O_2$ for reaction so that high yields of methanol can be generated while reducing or minimizing the production of other oxidation products, such as $CO_2$.

Example 3

Temperature Variations

This example provides additional illustration of the impact of temperature on the oxidation reaction. 3 mL of acetonitrile was loaded to the reactor and then gases were cold fed at −35° C., including 7 mmol of $O_2$, 118 mmol of $CH_4$ and 163 mmol of neutral gas (He or $N_2$). The pressure in the reactor after loading the gases at −35° C. was roughly 10 MPa-a. The reactor was then heated at a 2.5° C./min ramp rate to achieve the target temperature shown in Table 5. This resulted in an increase in the reactor pressure. The pressure values shown in Table 5 correspond to the calculated pressures based on an ideal gas law calculation, using the initial pressure at −35° C. as the basis for determining the final pressure in the constant reactor volume. After heating to the target temperature, the reactor was allowed to cool by natural convection without dwell time at the target temperature.

TABLE 5

Temperature Dependence of Conversion

| Pressure | T (° C.) | MeOH yield (CH$_4$ basis) | MeOH yield (O$_2$ basis) | CO$_2$ selectivity | O$_2$ conversion |
|---|---|---|---|---|---|
| 26.9 MPa-a | 250 | 0.04 | 0.3 | 50 | 0.8 |
| 28.3 MPa-a | 275 | 0.5 | 4.6 | 15 | 5.4 |
| 29.6 MPa-a | 300 | 0.72 | 6$^{+/-0.8}$ | 80 | 30 |

In addition to methanol yield relative to moles of CH$_4$ or O$_2$ in the reaction environment, Table 5 also provides CO$_2$ selectivity (yield) relative to CH$_4$ and O$_2$ conversion. As shown in Table 5, at the substantially supercritical conditions including a temperature of 250° C., only a modest amount of methanol was formed. The amount of CO$_2$ formed was comparable to or greater than the amount of methanol, but the main result was that little or no conversion of any type is occurring. This was confirmed by the relatively small percentage of O$_2$ that was converted. At 275° C., so that the acetonitrile was supercritical, the methanol yield was higher and the amount of CO$_2$ formed corresponded to only 15 vol % of the reaction products. Under these conditions, the yield of methanol versus other products is believed to be relatively high. Further increasing the temperature to 300° C. results in additional methanol production, but the majority of the conversion product (80 vol %) corresponds to CO$_2$. Thus, even though more methanol is being produced, a substantial amount of CH$_4$ and O$_2$ were converted to CO$_2$, as opposed to being available for processing again under the reaction conditions. Depending on the availability of methane, it could be a desirable trade-off to improve single-pass conversion rate in exchange for additional conversion of methane to CO$_2$ (and/or other non-methanol oxidation products).

Example 4

Solvent to Oxygen Ratio

This example illustrates the impact of the solvent to oxygen ratio in the reaction environment. 3 mL of acetonitrile was loaded into the reactor and then gases were cold fed at −35° C., including 163 mmol of He gas loading, 113-124 mmol CH$_4$ loading, and 6.7-7.4 mmol of O$_2$. The pressure in the reactor after loading the gases at −35° C. was roughly 10 MPa-a. The reactor was then heated at a 2.5° C./min ramp rate to achieve a target temperature of 275° C. After heating to the target temperature, the reactor was allowed to cool by natural convection without dwell time at the target temperature. Table 6 shows the results at the different solvent to oxygen molar ratio values. As shown in Table 6, the CH$_4$ to O$_2$ molar ratio is roughly 16:1.

TABLE 6

Solvent to Oxygen Ratio

| MeCN (mmol) | CH$_4$ (mmol) | O$_2$ (mmol) | Ratio of Solvent:O$_2$ | MeOH yield (%) O$_2$ based |
|---|---|---|---|---|
| 10 | 124 | 7.4 | 1.3 | 0.2 |
| 20 | 123 | 7.3 | 2.6 | 0.6 |
| 38 | 120 | 7.3 | 5.2 | 3 |
| 57 | 118 | 7.3 | 8 | 4.6 |

As shown in Table 6, at solvent:O$_2$ ratios near 1, the amount of solvent appears to be insufficient to activate the O$_2$ for the oxidation reaction. Increasing the solvent:O$_2$ ratio to 2.6 results in some additional activity. However, the improved yields of methanol relative to the amount of oxygen were not observed until the molar ratio of solvent to O$_2$ was greater than about 5. Further increases in the solvent to O$_2$ ratio resulted in additional methanol yield relative to the amount of oxygen.

Example 5

Solvent Type

This example provides an illustration of the impact of the nature of the solvent on the oxidation reaction. Instead of using only acetonitrile as a solvent, a series of different solvents was used. In this example, the reaction conditions corresponded to a temperature of 275° C. or 300° C., with a pressure of roughly 28 MPa-a. This was sufficient to provide supercritical conditions for acetonitrile and the acetonitrile derivatives and CO$_2$. However, the critical point of water is roughly 375° C. Due to the known oxidation pathway for methanol to convert to CO$_2$ rapidly at temperatures greater than 300° C., it was decided that the better comparison was to compare with water as a solvent at the same temperature, as increasing the temperature sufficiently to form supercritical water would be expected to result in substantially no methanol production (i.e., all methanol would be converted to CO$_2$).

For the acetonitrile and deuterated acetonitrile runs shown in Table 7, 3 mL of solvent was loaded into the reactor along with 7 mmol of O$_2$, 118 mmol of CH$_4$ and 163 mmol of neutral gas (He or N$_2$) at −35° C. The reactor was then heated at a 2.5° C./min ramp rate up to 300° C., followed by cooling (zero dwell time) back to ambient via natural convection.

For fluoroacetonitrile as the solvent, 17 mmol of solvent was loaded to the reactor along with 7 mmol of O$_2$, 118 mmol of CH$_4$ and 163 mmol of neutral gas (He or N$_2$) at −35° C. The reactor was then heated at a 2.5° C./min ramp rate up to 300° C., followed by cooling (zero dwell time) back to ambient via natural convection.

For trichloroacetonitrile as a solvent, a mixture of trichloroacetonitrile in acetonitrile in 1:10 ratio, corresponding to a total of 3 mL solution, was loaded into the reactor. The gases were then cold fed at −35° C., including 7 mmol of O$_2$, 118 mmol of CH$_4$ and 163 mmol of neutral gas (He or N$_2$). The reactor was then heated at a 2.5° C./min ramp rate up to 300° C., followed by cooling (zero dwell time) back to ambient via natural convection.

For water as a solvent, 3 mL of water was loaded into the reactor and gases were cold fed into the reactor at −35° C. corresponding to 22 mmol of O$_2$, 72 mmol of CH$_4$, and 114 mmol of N$_2$. The reactor was then heated at about 2.5° C./min ramp rate up to 300° C. The reactor was then allowed to dwell at 300° C. for roughly 3 hours, followed by cooling back to ambient via natural convection.

For CO$_2$ as the solvent, 118 mmol of CH$_4$, 7 mmol of O$_2$, 57 mmol of CO$_2$, and 103 mmol of He were cold fed into the reactor at −35° C. The reactor was then heated up to 275° C. at a roughly 2.5° C./min ramp rate (zero dwell time), followed by cooling to ambient via natural convection.

TABLE 7

Solvent Effect on Stabilization of Product

| Solvent | MeOH yield (%) $O_2$ based |
|---|---|
| MeCN | 4.6 |
| Deuterated Acetonitrile | 3 |
| Fluoroacetonitrile | 4 |
| Trichloroacetonitrile | 1 |
| Water | 0.4 |
| $CO_2$ | 0.5 |

As shown in Table 7, all of the acetonitrile derivatives provided improved methanol yield, relative to the molar amount of $O_2$, in comparison with using water at elevated pressure and temperature.

Example 6

Boron Nitride as an Initiator

It has been unexpectedly discovered that the yield of methanol can be further enhanced by using boron nitride as an initiator. Table 8 shows results from use of boron nitride with various amounts of acetonitrile solvent. In the runs shown in Table 8, the desired amount of acetonitrile was loaded into the reactor along with either 200 mg or 400 mg of boron nitride. The boron nitride had an initial surface area of roughly 100 m²/g. Then gases were cold fed at −35° C., including 7 mmol of $O_2$, 118 mmol of $CH_4$ and 163 mmol of neutral gas (He or $N_2$). The reactor was then heated up to 275° C. at a roughly 2.5° C./min ramp rate (zero dwell time), followed by cooling to ambient via natural convection.

TABLE 8

Boron Nitride as an Initiator

| MeCN (mmol) | Ratio BN SA (m²) to mmoles $O_2$ | Stirring (rpm) | MeOH yield (%) $O_2$ based |
|---|---|---|---|
| 57 | 2.8 | 0 | 5.2 |
| 57 | 2.8 | 60 | 7.8 |
| 0 | 2.8 | 60 | 3 |
| 57 | 5.7 | 60 | 17 |

It is noted that 57 mmol of acetonitrile corresponds to the typical amount added in most of the examples, and provided a solvent to $O_2$ molar ratio of roughly 8:1. As shown in Table 8, addition of boron nitride as an initiator without stirring resulted in a modest increase of methanol yield from roughly 4.6 mole % to roughly 5.2 mole % relative to the amount of $O_2$. (Compare, for example, with final row of Table 6 or middle row of Table 5.) With stirring, the methanol yield increased to 7.8 mole %. It is noted that even without the presence of the acetonitrile solvent, the boron nitride initiator was able to generate a 3 mole % yield of methanol relative to the amount of $O_2$. This is in contrast to the first row of Table 6, which showed little or substantially no conversion at a solvent to $O_2$ ratio of roughly 1.0.

Table 8 also shows that increasing the available initial surface area of boron nitride relative to the amount of $O_2$ initially results in a substantial increase in the yield of methanol (relative to $O_2$) of from 7.8 mol % to 17 mol %. It has been further discovered that having a beneficial ratio of initial surface area of boron nitride relative to the molar amount of $O_2$ results in an unexpected yield enhancement. This is illustrated in the FIGURE, which shows the yield of methanol relative to the molar ratio of boron nitride to $O_2$.

As shown in the FIGURE, the yield of methanol has a peak at a molar ratio of boron nitride to $O_2$ of roughly 2.3. More generally, an unexpectedly high yield of methanol can be achieved at molar ratios of boron nitride to $O_2$ of 1.8 to 2.8, or 2.0 to 2.6. As noted in the FIGURE, the standard deviation for the methanol yield relative to $O_2$ is roughly 0.2.

The data in the FIGURE is based on the molar ratio of boron nitride to $O_2$. It is believed that the relevant factor is actually the ratio of initial surface area for the nitride to millimoles of $O_2$. The initial surface area of the boron nitride (prior to exposure to supercritical conditions) used in the experiments to generate the FIGURE was roughly 100 m²/g. Based on the initial surface area of the boron nitride, the values shown in the FIGURE can be converted to the ratio of boron nitride initial surface area (in m²) to millimoles of $O_2$ by multiplying the values shown in the FIGURE by roughly 2.48. Thus, based on the FIGURE, the yield of methanol has a peak at a ratio value of roughly 5.7 square meters of boron nitride initial surface area in the reaction environment per millimole of $O_2$ in the reaction environment. More generally, an unexpectedly high yield of methanol can be achieved at ratios of boron nitride initial surface area to millimoles of $O_2$ between 4.5 and 7.0 m² BN (SA)/mmole $O_2$, or between 5.0 and 6.5 m² BN (SA)/mmole $O_2$. Without being bound by any particular theory, it is believed that boron nitride provides active sites that can facilitate the oxidation reaction. It is further believed that having an excess of boron nitride initial surface area results in an excess of available boron nitride active sites, resulting in over-oxidation of the resulting methanol product.

As a practical matter, in a commercial scale reactor, a method of distributing boron nitride throughout the volume occupied by a supercritical fluid would be beneficial. This can be achieved, for example, by supporting boron nitride on some type of support. Table 9 shows the results from using boron nitride supported on various types of refractory supports as an initiator in the reaction environment. For the data shown in Table 9, 200 mg of boron nitride was supported on alumina, silica, titania, or graphite. The alumina was a gamma alumina with a surface area of roughly 270 m²/g. The silica was a commercially available silica with a surface area of roughly 300 m²/g. The titania was a commercially available titania with a surface area of roughly 250 m²/g. The graphite had a surface area of roughly 60 m²/g.

In the runs shown in Table 9, 57 mmol of acetonitrile was loaded into the reactor along with the supported boron nitride. Then gases were cold fed at −35° C., including 7.8-13.5 mmol of $O_2$, 117-128 mmol of $CH_4$ and 163-197 mmol of neutral gas (He). The reactor was then heated up to 275° C. at a roughly 2.5° C./min ramp rate (zero dwell time), followed by cooling to ambient via natural convection. It is noted that the methanol yields in Table 9 are impacted by the fact that higher amounts of $O_2$ were used as compared with the results shown in Table 8.

TABLE 9

Supported Boron Nitride as an Initiator

| Catalyst | Stirring (rpm) | MeOH yield (%) $O_2$ based |
|---|---|---|
| BN-$Al_2O_3$ | 60 | 0.06 |
| BN-$SiO_2$ | 60 | 3.6 |
| BN-$TiO_2$ | 60 | 0.02 |
| BN-graphite | 60 | 3.9 |

As shown in Table 9, the boron nitride activity has an unexpected dependence on the nature of the support. Boron nitride supported on silica or graphite provides good yields of methanol, while boron nitride supported on alumina or titania results in a substantial decrease in methanol production relative to not having a catalyst.

Without being bound by any particular theory, it is believed that the differences in alcohol yield shown in Table 9 are due in part to Strong Support Metal Interaction (sometimes referred to as SMSI). For support materials with strong support metal interaction, the nature of the support material can interfere with the activity of a supported metal. As shown in Table 9, alumina and titania are examples of materials with SMSI behavior. Based on the results shown in Table 9, other materials that are expected to not be suitable as an initiator support include ceria, zirconia, and combinations of the various materials with SMSI behavior. By contrast, as shown in Table 9, silica and graphite are support materials that only weakly interact with the boron nitride initiator. Based on the results in Table 9, other materials that are believed to be suitable as an initiator support include, but are not limited to, molybdenum sulfide, tungsten sulfide, carbon nanotubes, doped carbon nanotubes (such as nitrogen doped carbon nanotubes). Combinations of silica, graphite, and/or other weakly interacting support materials are also believed to be suitable as support materials.

The boron nitride used in this example corresponded to hexagonal boron nitride (h-BN). In various aspects, other types of boron nitride that can be suitable for use as an initiator include, but are not limited to, boron nitride nanotubes; cubic boron nitride; wurtzite form of boron nitride; boron nitride aerogel foams; wires, arrays, and/or nanorods of boron nitride; amorphous BN; and combinations thereof.

Example 7

Additional Nitride Initiators

It has been further discovered that other types of nitrides can also act as an initiator, when a suitable amount of initial surface area for the nitride is provided. Table 10 shows data from use of various types of nitrides as potential initiators for methanol formation.

In the runs shown in Table 10, 57 mmol of acetonitrile was loaded into the reactor along with 200 mg of the nitride initiator. Then gases were cold fed at −30° C., including 7.0 mmol of $O_2$, 118 mmol of $CH_4$ and 163-197 mmol of neutral gas (He). The reactor was then heated up to 275° C. at a roughly 2.5° C./min ramp rate (zero dwell time) with stirring at 60 rpm, followed by cooling to ambient via natural convection.

TABLE 10

Nitride Initiators

| Catalyst | Initial Surface Area | MeOH yield (%) $O_2$ based |
|---|---|---|
| Carbon Nitride | ~100 m$^2$/g | 0.4 |
| Indium Nitride | <5 m$^2$/g | 1.7 |
| Boron Nitride | ~100 m$^2$/g | 7.8 |
| Titanium Nitride | <5 m$^2$/g | 0.8 |

The carbon nitride shown in Table 10 had an initial surface area of roughly 100 m$^2$/g. The carbon nitride also had a similar hexagonal morphology. However, adding the carbon nitride to the reaction environment resulted in a substantial reduction in methanol yield relative to the amount of $O_2$. (For comparison, the yield of methanol without any initiator under these conditions was 4.6%.) The yield when using indium nitride or titanium nitride was also less favorable relative to the boron nitride results.

Example 8

Methanol Yield Versus Dwell Time

This example provides an illustration of the impact of the nature of the solvent on the oxidation reaction. Additionally, the impact of including a copper-containing catalyst was also studied.

In this example, 3 mL of acetonitrile was loaded into the reactor. The reactor was cold fed with 22 mmol of $O_2$, 72 mmol of $CH_4$, and 114 mmol of $N_2$. The gases were fed at −35° C. including 28 mmol of $O_2$, 100 mmol of $CH_4$, and 160 mmol of $N_2$. The reactor was then heated at about 2.5° C./min ramp rate up to 300° C. The reactor was then allowed to cool immediately (no dwell time), or the reactor remained heated for the desired dwell time followed by cooling. Table 11 shows the variation in methanol yield based on dwell time.

TABLE 11

Methanol Yield versus Dwell Time

| System | Dwell time (h) | MeOH yield (%) $O_2$ based |
|---|---|---|
| Acetonitrile | 3 | 0.1 |
| Acetonitrile | 0 | 1.5 |

As shown in Table 11, allowing the reactor to remain at the supercritical conditions for an extended period of time resulted in a substantial loss in methanol yield.

Example 9

Ethane Conversion

It has been discovered that ethane can also be oxidized under supercritical conditions to produce alcohols (as oppose to oxidizing past the alcohol structure). Surprisingly, it was unexpectedly discovered that the yield of ethanol was greater than the yield of methanol. Due to this roughly 40 kJ/mol difference in the bond enthalpy of the carbon-hydrogen bonds in ethane relative to the carbon-carbon bond, it was expected that direct oxidation would be strongly selective for breaking of the carbon-carbon bond, resulting in preferential formation of methanol rather than ethanol. However, it has been discovered that the direct oxidation environment described herein allows for formation of ethanol in greater yield than methanol. It was further discovered that the total yield of alcohol (methanol plus ethanol) from ethane conversion was greater than the total methanol yield from methane conversion.

Table 12 shows results oxidation of methane and ethane in the presence of boron nitride in a supercritical acetonitrile environment. In the runs shown in Table 12, the desired amount of acetonitrile was loaded into the reactor along with 200 mg of boron nitride. The boron nitride had a surface area of roughly 100 m$^2$/g. Then gases were cold fed at −35° C., including 13.5 mmol of $O_2$, either 118 mmol of $CH_4$ or 15.8 mmol $C_2H_6$, and 163 mmol of neutral gas (He). The reactor was then heated up to 275° C. at a roughly 2.5° C./min ramp rate (zero dwell time), followed by cooling to ambient via natural convection. This corresponds to an acetonitrile to $O_2$ ratio of roughly 4:1.

TABLE 12

Methane versus Ethane Conversion

| MeCN (mmol) | Type of Hydrocarbon | Stirring (rpm) | Alcohol yield (%) $O_2$ based |
|---|---|---|---|
| 57 | Methane | 60 | 6.5 |
| 57 | Ethane | 60 | 8.1 (3.6 MeOH, 4.5 EtOH) |

As shown in Table 12, under similar reaction conditions, the total alcohol yield from oxidation of ethane was greater than the total alcohol yield from oxidation of methane. Additionally, ethanol was unexpectedly formed in a higher yield of 4.5 mole % as compared with the 3.6 mole % yield of methanol, relative to the molar amount of $O_2$ in the reaction environment.

The results in Table 12 also generally confirm that ethanol can be converted into alcohols in a supercritical environment. Additionally, based on the successful conversion of ethanol in the presence of boron nitride, it is believed that the yield of alcohol from conversion of ethanol in the presence of boron nitride would show a similar peak at ratios in the reaction environment of boron nitride surface area (in square meters) to millimoles of $O_2$ between 4.5 and 7.0 m$^2$ BN (SA)/mmole $O_2$, or between 5.0 and 6.5 m$^2$ BN (SA)/mmole $O_2$.

All patents, test procedures, and other documents cited herein, including priority documents, are fully incorporated by reference to the extent such disclosure is not inconsistent with this invention and for all jurisdictions in which such incorporation is permitted. Should the disclosure of any of the patents and/or publications that are incorporated herein by reference conflict with the present specification to the extent that it might render a term unclear, the present specification shall take precedence.

As should be apparent from the foregoing general description and the specific embodiments, while forms of the invention have been illustrated and described, various modifications can be made without departing from the spirit and scope of the invention. Accordingly, it is not intended that the invention be limited thereby. Many variations will suggest themselves to those skilled in this art in light of the above detailed description. All such variations can be within the full intended scope of the appended claims. Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

The invention claimed is:

1. A method for partial oxidation of ethane comprising: contacting ethane with $O_2$ in the presence of acetonitrile in a reaction environment, under supercritical conditions for acetonitrile, to form methanol and ethanol, the supercritical conditions comprising a temperature of 310° C. or less,
wherein a molar amount of ethanol formed is greater than a molar amount of methanol formed.

2. The method of claim 1, wherein the ethane is contacted with $O_2$ in the absence of a catalyst.

3. The method of claim 1, wherein the $O_2$ is contacted with the methane under at least one of supercritical conditions and substantially supercritical conditions for a residence time of 0.1 seconds or more, a residence time of 10 minutes or less, or a combination thereof.

4. The method of claim 1, wherein a molar ratio of ethane to methane in the reaction environment is 4.0 or more.

5. The method of claim 1, wherein the reaction environment comprises 10 mole % or less of $H_2O$.

6. The method of claim 1, wherein the yield of methanol is 1.0 mole % or more relative to the molar amount of $O_2$ in the reaction environment, or wherein the yield of ethanol is 1.0 mole % or more relative to the molar amount of $O_2$ in the reaction environment, or a combination thereof.

7. The method of claim 1, wherein the supercritical conditions comprise a temperature of 300° C. or less.

8. The method of claim 1, wherein the molar ratio of ethane to $O_2$ is 2.0 or more.

9. A method for partial oxidation of alkanes comprising: contacting methane, ethane, or a combination thereof with $O_2$ in the presence of acetonitrile and boron nitride in a reaction environment, under supercritical conditions for acetonitrile, to form methanol, the supercritical conditions comprising a temperature of 300° C. or less, wherein the boron nitride is supported on graphite, $SiO_2$, or a combination thereof.

10. The method of claim 9, wherein the $O_2$ is contacted with the methane under at least one of supercritical conditions and substantially supercritical conditions for a residence time of 0.1 seconds or more, or a residence time of 10 minutes or less, or a combination thereof.

11. The method of claim 9, wherein the reaction environment comprises 10 mole % or less of $H_2O$.

12. The method of claim 9, wherein the yield of methanol is 1.0 mole % or more relative to the molar amount of $O_2$ in the reaction environment, or wherein the yield of ethanol is 1.0 mole % or more relative to the molar amount of $O_2$ in the reaction environment, or a combination thereof.

13. The method of claim 9, wherein a molar ratio of ethane to methane in the reaction environment is 4.0 or more.

14. The method of claim 9, wherein the molar ratio of methane to $O_2$ is 2.0 or more.

15. A method for partial oxidation of alkanes comprising: contacting methane, ethane, or a combination thereof with $O_2$ in the presence of acetonitrile and a nitride initiator in a reaction environment under supercritical conditions for acetonitrile to form methanol, the supercritical conditions comprising a temperature of 300° C. or less, wherein a ratio of initial surface area of the boron nitride to a molar amount of $O_2$ in the reaction environment is 4.5 to 7.0 m$^2$ BN (SA)/mmole $O_2$.

16. The method of claim 15, wherein the $O_2$ is contacted with the methane under at least one of supercritical conditions and substantially supercritical conditions for a residence time of 0.1 seconds or more, or a residence time of 10 minutes or less, or a combination thereof.

17. The method of claim 15, wherein the reaction environment comprises 10 mole % or less of $H_2O$.

18. The method of claim 15, wherein the yield of methanol is 1.0 mole % or more relative to the molar amount of $O_2$ in the reaction environment, or wherein the contacting further forms ethanol, a yield of ethanol being 1.0 mole % or more relative to the molar amount of $O_2$ in the reaction environment, or a combination thereof.

19. The method of claim 15, wherein a molar ratio of ethane to methane in the reaction environment is 4.0 or more.

20. The method of claim 15, wherein the molar ratio of methane to $O_2$ is 2.0 or more.

\* \* \* \* \*